United States Patent [19]
Kobiki et al.

[11] Patent Number: 5,278,886
[45] Date of Patent: Jan. 11, 1994

[54] RADIOSURGERY EFFECTING POSITION CORRECTION OF COLLIMATOR

[75] Inventors: Takaaki Kobiki, Noda; Akira Ohgushi, Tokyo, both of Japan

[73] Assignee: Hitachi Medical Corporation, Tokyo, Japan

[21] Appl. No.: 729

[22] Filed: Jan. 5, 1993

[30] Foreign Application Priority Data

Jan. 16, 1992 [JP] Japan ................... 4-025799

[51] Int. Cl.$^5$ .............................................. A61N 5/10
[52] U.S. Cl. ...................................... 378/65; 378/151
[58] Field of Search .............. 378/65, 151; 250/492.3

[56] References Cited
U.S. PATENT DOCUMENTS

5,189,687 2/1993 Bova et al. .................... 378/65

*Primary Examiner*—Craig E. Church
*Attorney, Agent, or Firm*—Antonelli, Terry, Stout & Kraus

[57] ABSTRACT

A stereotactic radiosurgery including a collimator adapted movably to an irradiation head, a driving apparatus for changing a position of the collimator while keeping a position relation in which a center line of a hole of the collimator coincides with a line connecting an apex of a radiation cone and a center portion of the focus, and a control apparatus for detecting a position error between an irradiating direction of the radiation and the center portion of the focus, driving the collimator driving apparatus and moving the collimator to a position at which the detected position error is offset.

10 Claims, 12 Drawing Sheets

RADIOSURGERY EFFECTING POSITION CORRECTION OF COLLIMATOR

BACKGROUND OF INVENTION

This invention relates to a stereotactic radiosurgery for effecting medical treatment by concentrating stereotactically a narrow beam of a radiation on one point. More particularly, the present invention relates to a stereotactic radiosurgery which will be suitable for correctly concentrating a radiation on one stereotactic point for a defect of mechanical accuracy of a gantry for irradiating a radiation and for any focuses.

An irradiation method of a radiation referred to as a "stereotactic method" has drawn an increasing attention. It is a method of medical treatment which imparts a high dose of a radiation to only a focus from multiple directions and destroys the focus. According to this method, the dose of the radiation to normal tissues around the destroyed focus is extremely small, and any adverse effects on the normal tissues can be eliminated.

Stereotactic radiosurgeries include a multi-beam source system radiosurgery referred to as a "Gamma Unit" and a mono-beam source system radiosurgery (PCT Japan Publication No. Hei-2-503521 (W089/05171) entitled "Stereotactic Radiosurgery System SRS 200 Isocentric Subsystem", PHILLIPS).

The former comprises a hemispherical collimator having a large number of irradiation holes and a cobalt 60 sealed beam source situated outside this collimator, and can accomplish medical treatment by applying concentratedly a gamma dose from a large number of cobalt 60 beam sources situated hemispherically to a focus. The latter rotates a gantry with the focus of a patient as a center by the use of an electron beam accelerator, etc, and can concentratedly irradiate the radiation to the focus from all directions while rotating a treatment couch. Accordingly, both can apply a large dose as an accumulated dose to the focus, and can reduce the dose to the normal tissue by a dispersion effect of the dose.

Figure 1:
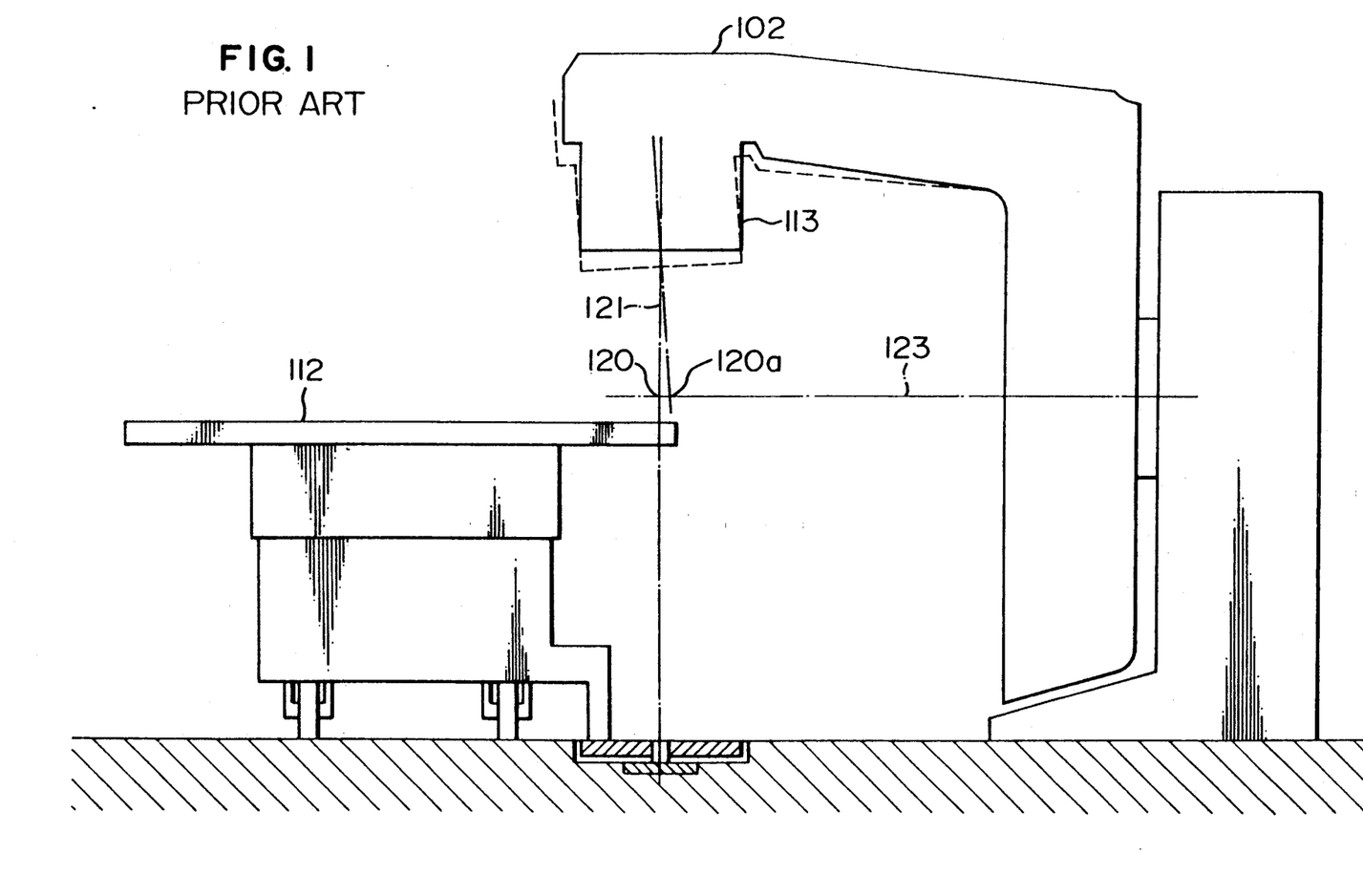
FIG. 1 is an explanatory view useful for explaining a position error in a stereotactic radiosurgery.
Figure 2:
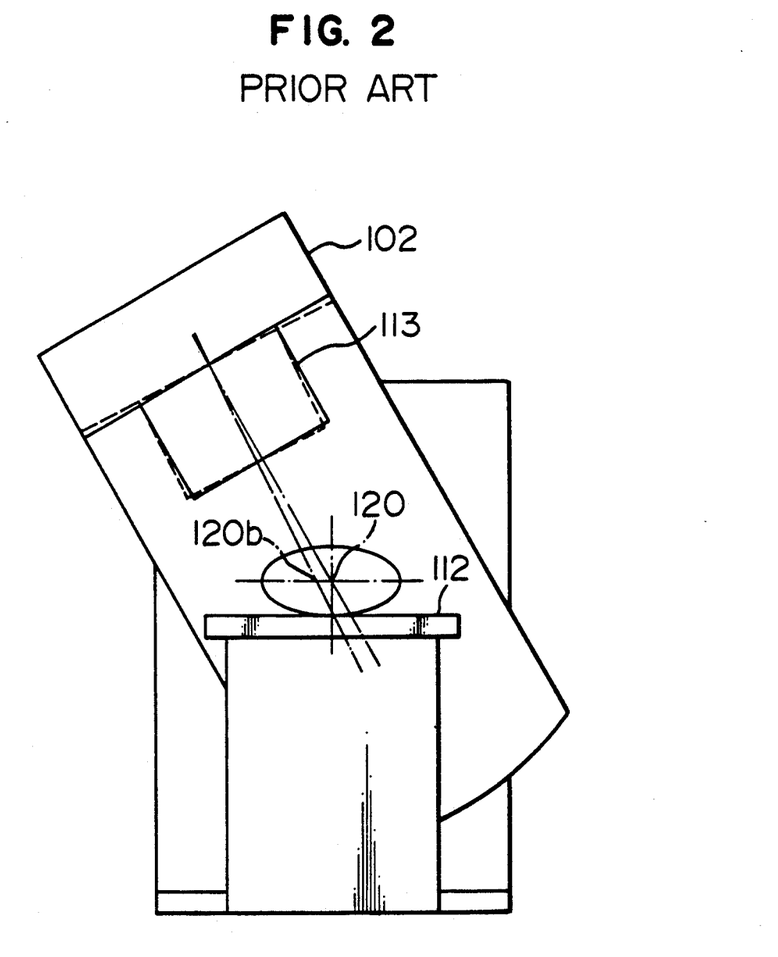
FIG. 2 is also an explanatory view useful for explaining a position error in a stereotactic radiosurgery.

However, the former uses a large number (about 200) of cobalt 60 as the beam source. Since cobalt 60 has half life, exchange becomes necessary, and problems of maintenance and management occur. Furthermore, since the cost of the apparatus is high, this system has not yet been wide spread. The Gamma Unit of this system is exclusively for the head, and is not suitable for the chest and the abdomen at which the focus moves with the respiration. Accordingly, stereotactic surgery using the electron beam accelerator according to the latter has been expected. Stereotactic radiosurgical treatment using the electron beam accelerator will be explained generally with reference to FIGS. 1 and 2. A gantry 102 of an electron beam accelerator rotates with a horizontal axis 123 being the center, and a beam passes through an irradiation head 113 mounted to the radiation gantry 102, and is narrowed and irradiated to a focus. A point of intersection 120 between the horizontal axis 123 and the beam center 121 irradiated by a collimator is an isocenter, and the focus of a patient is brought into conformity with this position. The beam center must always catch the point of intersection 120 even while the gantry 102 is rotating with the horizontal axis 123 being the center. The radiation can be irradiated to the focus from all directions by operating in a composite way the rotation of the gantry 102 and the rotation of a treatment couch 112 inside a horizontal plane.

The gantry and the irradiation head mounted to the gantry are very heavy. Therefore, if any shake or deflection occurs during the rotation of the gantry as indicated by dotted line in FIGS. 1 and 2, the beam center cannot catch the focus and the focus of the radiation beam does not pass through the isocenter as represented by reference numerals 120a and 120b. When the medical treatment is carried out under such a state, the ratio of the dose to the focus and the dose to the normal tissue becomes small, so that the destroying effect of the focus becomes also small and even the normal tissue might be destroyed. Moreover, followup performance of the irradiation head, which is a heavy device, with the chest and the abdomen moving with the respiration is low, and the system must be increased in scale to accomplish this operation.

SUMMARY OF THE INVENTION

It is an object of the present invention to provide a stereotactic radiosurgery which enables a radiation beam to correctly catch a focus even when a gantry having an irradiation head is rotating.

In a stereotactic radiosurgery comprising a treatment couch rotating on a horizontal plane with an isocenter being the center, a gantry rotating on a perpendicular plane with the isocenter being the center, an irradiation head supported by the gantry and appropriately irradiating a radiation towards the isocenter and a collimator for guiding the radiation emitted from the irradiation head to the isocenter through a collimator hole, the object described above can be accomplished by a stereotactic radiosurgery which includes a link mechanism for driving the collimator and a positioning mechanism for controlling the position of the collimator, and wherein a position error of the radiation from an irradiating direction of the radiation from the head with the rotation of the gantry is detected and the collimator is movably controlled so as to offset this position error.

The position error in the irradiation direction of the radiation is measured by an optical measuring instrument such as a laser, a correction value of the position of the collimator is calculated from this measurement value, and correction is made by the positioning mechanism.

Another method of correcting the position error comprises determining in advance a relationship between a rotating angle of the gantry and the position error, storing the relationship as a table in a memory, and effecting position correction of the collimator by referring to the table with the rotation of the gantry.

When any position error of the focus occurs due to the respiration, the present invention effects position control of the collimator in such a manner as to direct the collimator hole towards the focus.

According to the present invention, the collimator is moved by the collimator driving apparatus and the position control apparatus when any position error from a stereotactic point occurs due to the shake or deflection during the rotation of the gantry, and the central axis of the collimator hole is brought into conformity with an apex of a radiation cone. According to this arrangement, the central axis of the radiation always passes through the isocenter, and moreover, the dose distribution of the radiation irradiated from the collimator hole becomes constant. In this way, the radiation can always be concentrated on the stereotactic point even during the rotation of the gantry.

The radiation can be irradiated to the focus moving with the respiration by moving the collimator in synchronism with the respiration by the collimator driving apparatus and the position control apparatus so that the central axis of the collimator hole is always coincident with a straight line connecting the apex of the radiation cone with the central point of the focus.

Therefore, a large dose as an accumulated dose can be applied to the focus but the dose to the normal tissue can be reduced due to the dispersion effect of the dose. As a result, adverse influences of the radiation on the normal tissue become smaller, the focus can be destroyed accurately, and the treatment effect by the radiation becomes maximal.

The radiation can be irradiated to the focus at the chest or the abdomen moving with the respiration such as a lung cancer by operating the collimator in such a manner as to follow up the movement of the focus. Therefore, radiosurgical treatment of the chest and the abdomen, that has been difficult conventionally, can be carried out more easily and safely.

DESCRIPTION OF THE PREFERRED EMBODIMENTS

Hereinafter, an embodiment of the present invention will be described with reference to the accompanying drawings.

Figure 3:
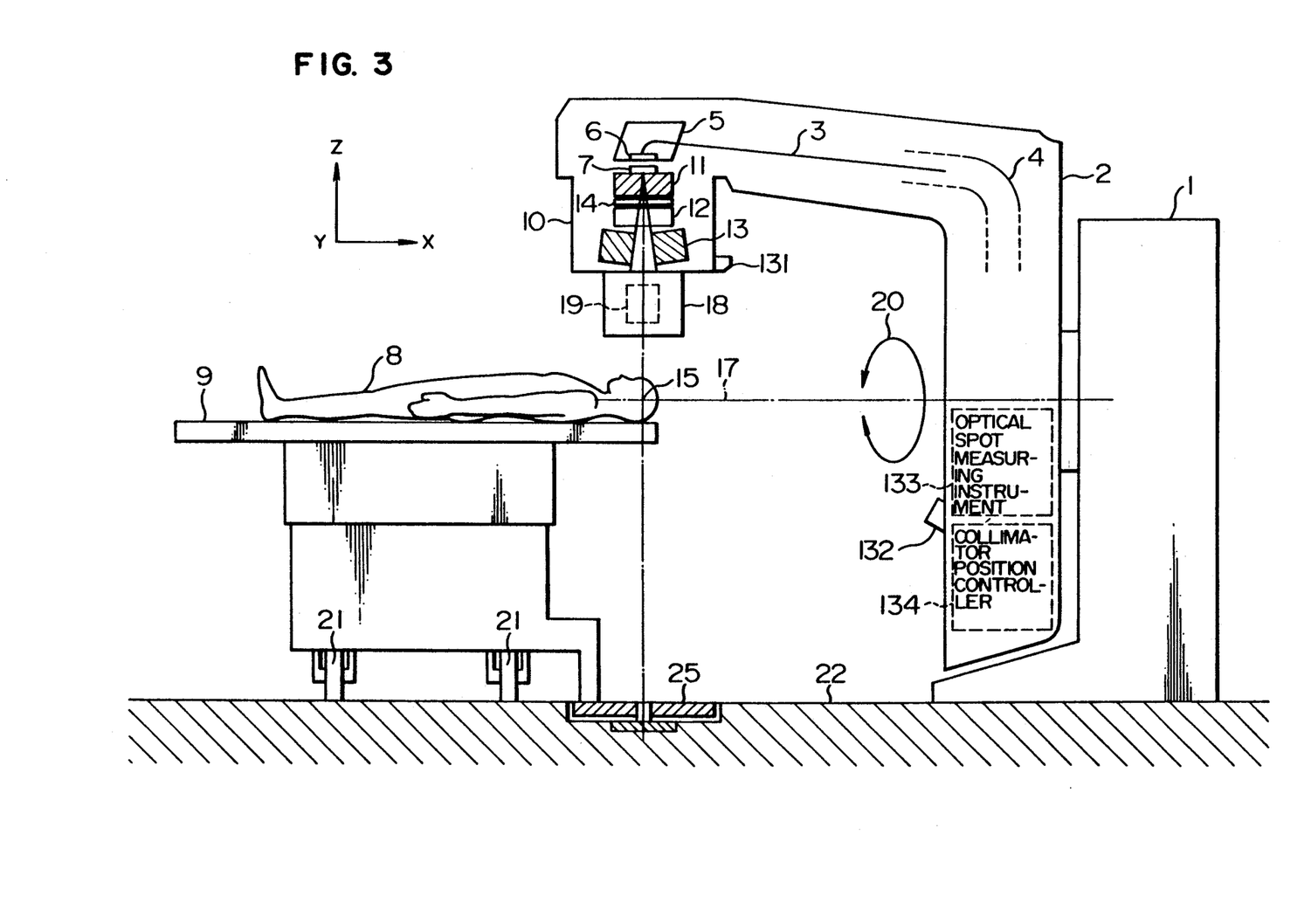
FIG. 3 is a schematic view showing an embodiment of a stereotactic radiosurgery according to the present invention.

FIG. 3 is an overall structural view of a stereotactic radiosurgery according to the present invention.

This stereotactic radiosurgery comprises a gantry 2 supported by a support 1 and rotating round a patient 8 as represented by an arrow 20, an irradiation head 10 supported by the gantry 2, a collimator driving apparatus 18 supported by the irradiation head 10, and a treatment couch 9 for supporting thereon the patient 8. The gantry 2 and the irradiation head 10 include a transfer path 4 for transferring an electron beam 3 from an electron beam generation source (not shown), a deflecting magnet 5 for deflecting the electron beam 3, a vacuum window 6 situated at an outlet portion of the electron beam 3, an X-ray target 7 for irradiating the X-ray upon being irradiated with the electron beam 3, a conical collimator 11 for contracting the irradiated X-ray, movable collimators 12 and 13 capable of operating in x and y directions, for converting the X-ray into a rectangular form, and a filter 14 interposed between the conical collimator 11 and the movable collimator 12. The filter 14 is a flattening filter that makes uniform an X-ray dose distribution inside a cone. A deflection quantity of the irradiation head 10 is measured by an optical spot position measuring instrument (103) comprising a laser generator 101 and a beam receiver 102 as a sensor. Reference numeral 104 denotes a position control unit for controlling the position of the collimator.

Under the state shown in FIG. 3, the point of intersection between a perpendicular axis 16 as an irradiation center of the X-ray and a horizontal axis 17 as a rotational center of the gantry 2 is an isocenter. To align a focus such as a tumor with this position, positioning is made by moving the treatment couch up and down and to the right and left. The treatment couch 9 is fixedly fitted to the peripheral portion of a rotary disc 25 situated in such a manner as to be capable of rotating by a predetermined angle on a horizontal plane with a perpendicular axis 16 passing through the isocenter 15 as the center. In this way, the treatment couch can rotate on the horizontal plane with the rotation of the rotary disc 25 with the isocenter 15 being the center. A truck 21 is situated for this rotation.

Each of the movable collimators 12 and 13 comprises two collimator plates, and a rectangular X-ray passage is defined by situating these four collimator plates in a rectangular form in the x and y directions. The size of the rectangular shape can be adjusted by changing the distances between the four collimator plates. However, the movable collimators 12, 13 play only the role of contracting the X-ray into the rectangular form but cannot correct a position error with respect to one stereotactic point. Therefore, a stereotactic collimator 19 is additionally situated between the irradiation head 10 and the isocenter 15. In this embodiment, the collimator 19 is accommodated in a casing (reference numeral 24 in FIG. 4), though it has been fixed to the irradiation head 10 in a conventional mono-beam source type. The casing 24 is fixed to the irradiation head, and has a built-in driving mechanism 18 for driving the collimator 19. The collimator 19 includes a collimate aperture (reference numeral 43 in FIG. 4) for further narrowing the radiation passing through the movable collimator 13. The collimator 19 can swing with a support point being the center and can be fixed (positioned) at any of its swing positions. Furthermore, the position of the swing support point lies at the apex of a radiation cone. The center line (reference numeral 29 in FIG. 4) of the collimate aperture exists on a straight line connecting the apex of the radiation cone and the isocenter so that the dose distribution of the radiation emitted from the collimate aperture is constant at whichever swing position the collimator 19 may exist. The term "radiation cone" hereby used means a radiation beam emitted from the target 7, and its apex represents the radiating position of the target 7. If the radiation source is a spot radiation source, the term "apex" indicates the position of the spot itself and if it is a plane radiation source, it indicates the central position of the plane.

The collimator driving apparatus 18 effects swinging of the collimator 19 and positioning of the collimator 19 to an arbitrary swing position in accordance with an instruction from the collimator position control unit 104. To this end, the driving apparatus 18 includes a link mechanism (symbol L in FIG. 4) for swinging the collimator 19 and a driving mechanism (symbol P in FIG. 4) for positioning. As will be described elsewhere in further detail, the driving apparatus 18 swings the collimator 19 in a direction for offsetting a position error and positions the collimator 19 at an offset position of the position error once the position error of the radiation in the irradiating direction is known. After this positioning is completed, emission of the radiation for the treatment is started.

Figure 4:
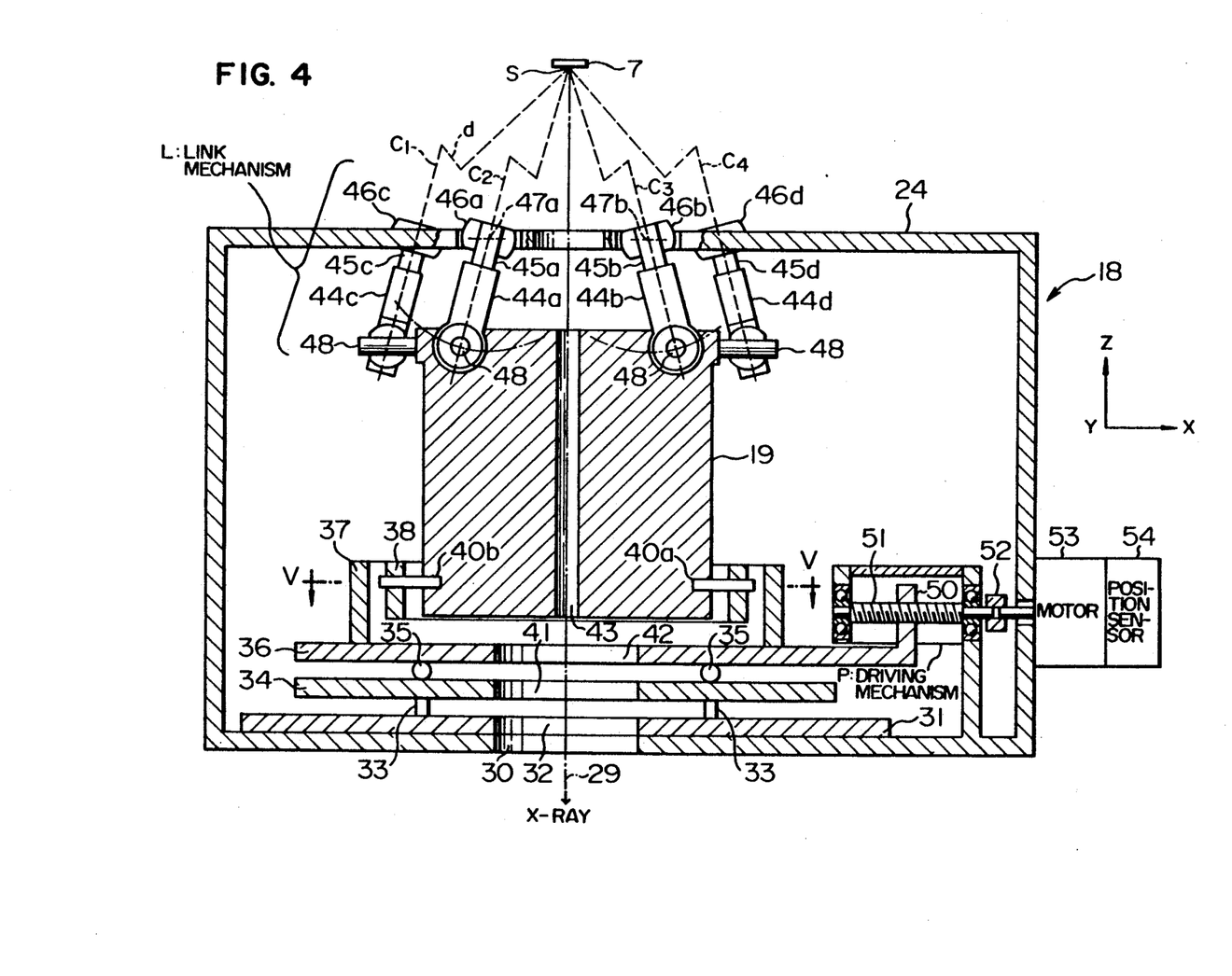
FIG. 4 is a sectional view showing an embodiment of a collimator and a driving apparatus in the present invention.
Figure 5:
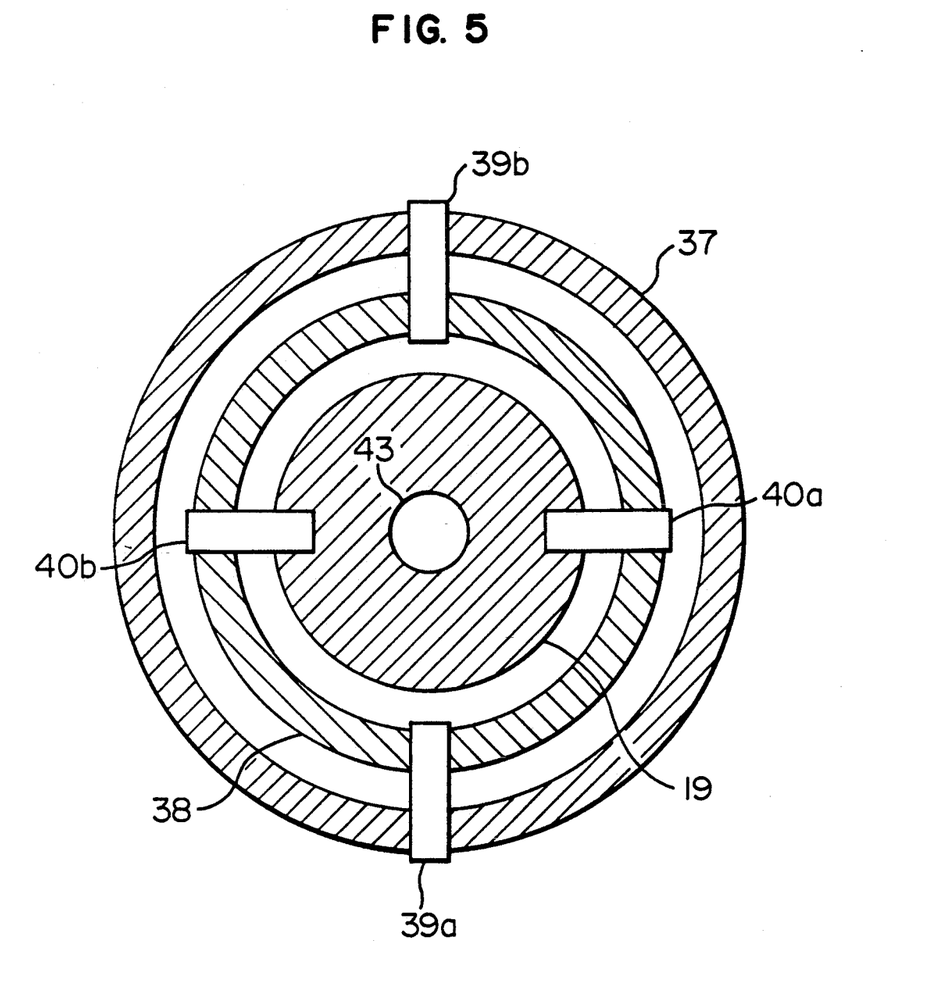
FIG. 5 is a sectional view taken along a line V—V of FIG. 4.

A definite embodiment of the collimator driving apparatus 18 and of the collimator 19 will be explained. FIG. 4 is a sectional view when the irradiation head is cut along a plane parallel to the sheet of the drawing, and FIG. 5 is a sectional view taken along a line V—V of FIG. 4. Eight link mechanisms L are situated above the collimator 19. (Only four of them on the foreground side are shown in the drawing). All these link mechanisms are constituted in such a manner that their center lines $C_1$ to $C_4$ (with $C_5$ to $C_8$ being omitted) cross one another on their extensions at the apex S (the apex of the radiation cone) on the target 7. (The $C_1$ to $C_4$ are represented by broken lines in the drawing for the sake of convenience.) The collimator 19 is allowed to swing with this apex S being the support point. Even when the collimator 19 swings, the point of intersection of the center lines $C_1$ to $C_4$ on their extension always exists at the apex S. Furthermore, the center line 29 of the collimate aperture of the collimator 19 always crosses the apex S on its extension even when the collimator 19 swings.

The driving mechanism P acts on the link mechanisms L, causes swinging sufficient to offset the position error, and fixes and positions the collimator 19 at the offset position.

The construction of the driving mechanism P will be explained. The casing 24 has a hole 30 as the passage port of the radiation, and a member 31 having a similar hole 32 is fixedly fitted to the casing 24. A planar member 34 is so fitted on the member 31 through a linear guide roller 33 as to be slidable in the y direction. Another planar member 36 is so fitted on the planar member 34 through another linear guide roller 35 as to be slidable in the x direction. In other words, these members 34 and 36 constitute an "X—Y table" that is known generally. The planar member 36 has an arm 50 fitted to a ball screw 51. When the ball screw 51 is rotated by a motor 53, the planar member 36 can be moved in the x direction. Its moving distance is detected by a position sensor 54. The planar member 34, too, has a similar independent moving mechanism (not shown) in the same way as the moving mechanism of the member 36, and can move in the y direction.

A large ring 37 having its center on the center line 29 of the collimate aperture 43 of the collimator 19 is fixed onto the planar member 36, and a medium ring 38 is situated inside the large ring 37. The collimator 19 is situated inside this medium ring. First support shafts 40a and 40b are situated on the collimator 19 and on the medium ring 38 on the same straight line as shown in FIG. 5. The support shafts 40a and 40b are fixed to the medium 38 but are not fixed to the collimator 19, but support and allow the collimator 19 to rotate with the support shafts 40a, 40b being the center. Second support shafts 39a and 39b are situated on the large ring 37 and on the medium ring 38 on the same straight line. These support shafts 39a and 39b are fixed to the large ring 37, but are not fixed to the medium ring 38. In other words, the shafts 39a and 39b support the medium ring 38 so that the medium ring 38 can rotate with the shafts 39a, 39b being the center. The axes of the first and second support shafts 40a, 40b and 39a, 39b are positioned on the same plane, and the first support shafts 40a, 40b and the second support shafts 39a, 39b are so situated as to criss-cross one another. This criss-cross arrangement allows the collimator 19 to incline in the x and y two-dimensional direction.

The operations of the large and medium ring 37, 38 will be explained with reference to FIG. 5.

The collimator is inclined by the link mechanisms with the movement of the X—Y table comprising the members 34 and 36. Therefore, the members 34 and 36 must also follow up the inclining motion of the collimator. The rings 37 and 38 permit a smooth inclining motion. In other words, whereas the members 34 and 36 cause parallel motion, the collimator is inclined by the link mechanisms. In this way, the large and medium rings so function as to move the collimator and to permit the smooth inclination.

A first shaft 48 protrudes from the upper side of the collimator 19 (towards the irradiation head), and rod ends 44 (a to d) fit to the first shaft. Second shafts 45 (a to d) protruding from the rod ends 44 are interconnected to spherical bearings 46 (a to d) fixed to the casing 24, respectively. The fitting relation of the link mechanism L constituted by all the rod ends 44, the second shaft 45 and the spherical bearings 46 is set in such a fashion that when the center line 29 of the hole 43 of the collimator 19 coincides with the perpendicular axis 16 shown in FIG. 3, the shaft centers $C_1$ to $C_4$ of the second shafts 45 pass through the apex S of the cone of the radiation, as depicted in FIG. 4. Though only four links are shown situated in FIGS. 4 and 6, four other links are also situated on the opposite side to the sheet of the drawings, and eight, in total, of the links constitute the link mechanism L.

Figure 6:
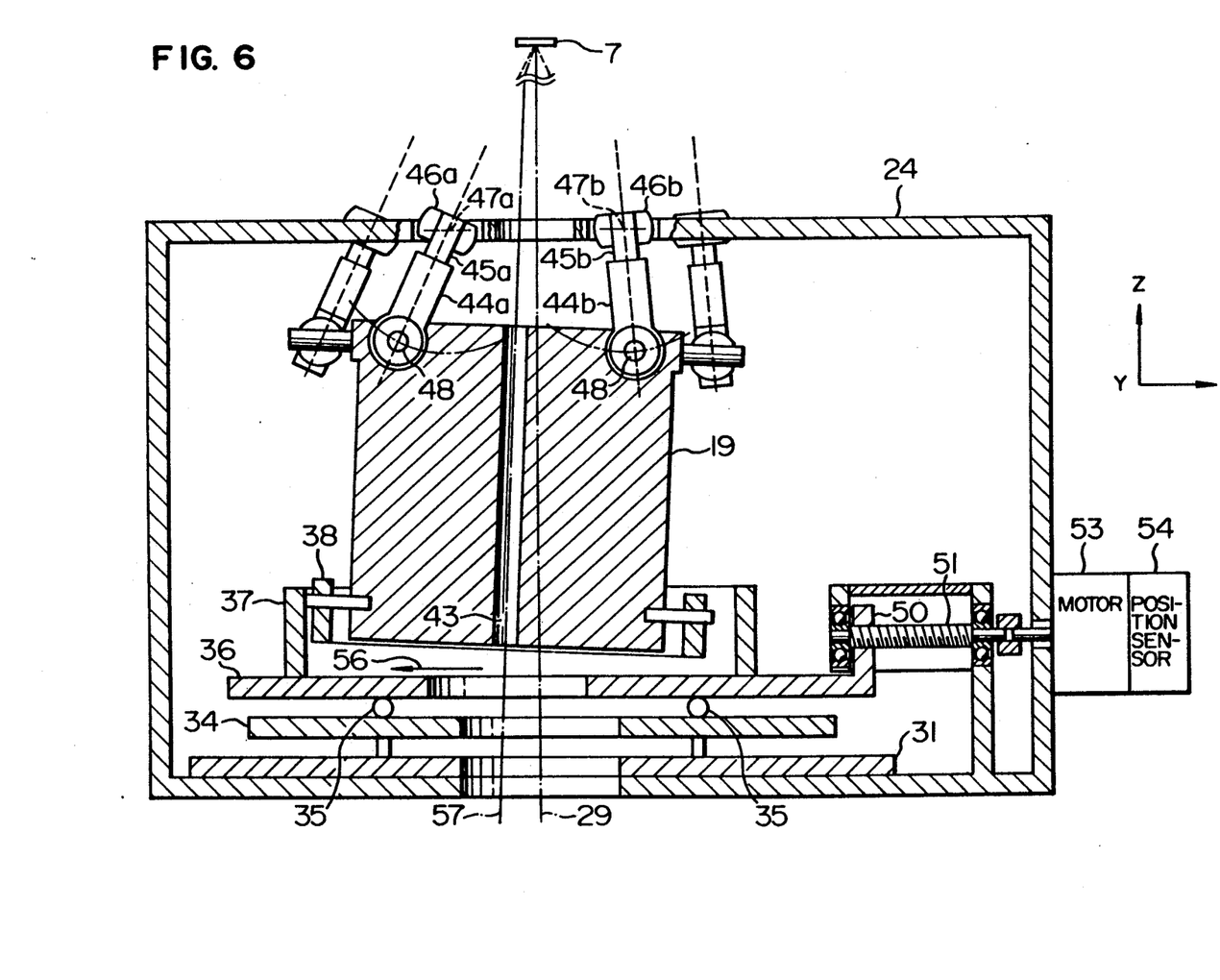
FIG. 6 is a schematic view showing an operation state of the collimator and the driving apparatus in the present invention.

Next, the operation by this construction will be explained with reference to FIG. 6. When the ball screw 51 is rotated by the revolution of the motor 53, the arm 50 fitting to the ball screw 51 moves in a direction indicated by an arrow 56. The member 36, too, causes parallel motion in parallel with the member 31 in the direction of the arrow 56 by means of the linear guide roller 35. The large ring 37 fixed to the member 36 moves similarly, as well. Accordingly, the collimator 19 causes parallel motion in the direction of the arrow 56 through the second support shafts 39a, 39b, the medium ring 38 and the first support shafts 40a, 40b. However, this parallel motion is restricted by the link mechanism comprising the rod ends 44a, 44b, the second shafts 45a, 45b and the spherical bearings 46a, 46b at the upper part of the collimator 19, and hence, the collimator 19 inclines as shown in FIG. 6. In this instance, rotation occurs in the link mechanism as it is allowed to swing with the support points 47a, 47b as the center, so that the collimator 19 inclines with the second support shafts 39a, 39b as its center. Accordingly, the medium ring 38, too, inclines relative to the large ring 37. This tilt angle is proportional to the moving distance of the member 36 and when it inclines, the center line 57 of the collimate aperture 43 always passes through the apex of the cone of the radiation. This is true of the case where the member 34 moves in a direction orthogonal to the sheet of the drawing, that is, in the y direction. In this case, the collimator 19 inclines with the first support shafts 40a, 40b being the center. Accordingly, the similar result can be obtained during the composite operation of the members 34 and 36, and according to the construction of the present invention, the center line of the collimate aperture always passes through the apex of the cone of the radiation when the collimator 19 inclines.

Figure 7:
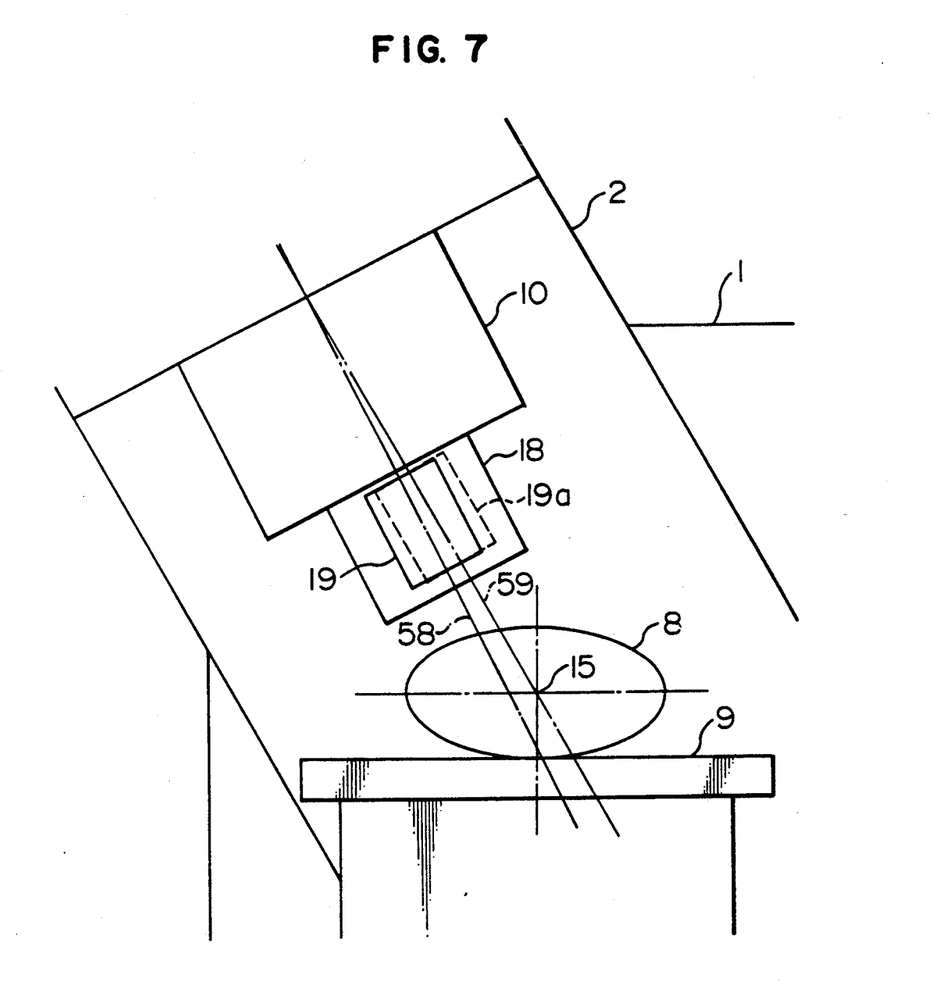
FIG. 7 is a schematic view showing a position error between the gantry and an irradiation head and an example of offset of the position error.

Accordingly, when the gantry 2 and the irradiation head 10 incline with their center axes lying on the collimator center line (radiation center), the collimator 19 is operated in the way described above and is inclined as typified by a collimator 19a at the position represented by a dash line, and in this way, the center axis 59 of the collimate aperture can be so corrected as to be coincident with a line connecting the apex of the radiation cone and the isocenter 15.

Figure 8:
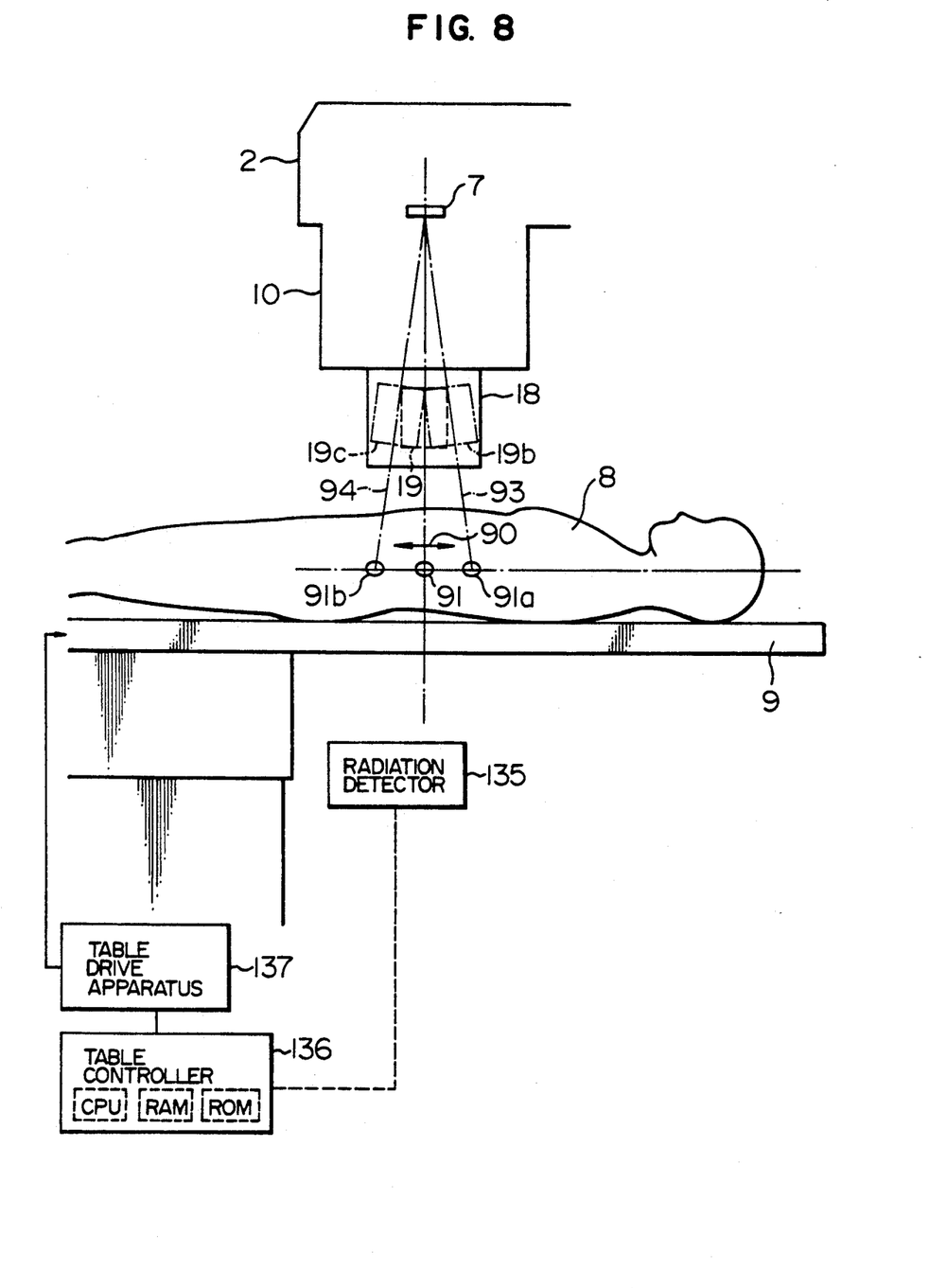
FIG. 8 is an explanatory view useful for explaining offset of the position error at the time of irradiation to a moving portion.

A focus which moves with the respiration, such as the chest or the abdomen, reciprocates and moves as indicated by 91a, 91b with the respiration as indicated by an arrow 90 even when the isocenter 15 is aligned with the focus as shown in FIG. 8. Therefore, the collimator 19 must be moved in such a manner as to follow up the motion of this focus. In this instance, the collimators 19b, 19c must be inclined in such a manner that the central axes of the holes of the collimators 19b, 19c are coincident with the straight lines 93, 94 connecting the apex of the cone of the radiation (the central point of the X-ray target in the case of the drawing) and the central point of the focus. This alignment can be accomplished easily by the use of the driving apparatus 18 described above.

The operation of the collimator position controller 104 will be explained with reference to FIG. 9. The collimator position controller 104 includes a CPU, an RAM, an ROM, an interface circuit, and so forth. To begin with, an embodiment wherein a position error of the gantry for each rotational position is measured in advance and is stored in the memory, and this position error is offsetted at the time of the irradiation, will be explained. Processing in this embodiment is accomplished by control using a microcomputer. A position error relative to the isocenter by a certain angle is measured in advance when the gantry rotates gradually, and the measurement data is stored as a measurement data table in the memory. The rotational angle data of the gantry is given to the measurement data table I for each certain predetermined sampling angle (step 60), and the measurement data is read out on the basis of this angle data (step 61). A correction value in which direction and by which distance is calculated so as to offset the position error (step 62) and the linear moving distance of the members 34 and 36 is determined (step 63). This linear moving distance is converted to the rotational quantity of the motor (step 64) and the motor is driven towards the target value of the rotational quantity thus Converted (step 65). Drive control of this motor, too, is effected by the collimator position controller 104 but does not rely on a feedback loop by ordinary speed control and position control by the position sensor (FIG. 6) such as shown in FIG. 10. In FIG. 10, a target position is first given (step 65A), and its difference from a position detection value which is fed back is calculated (step 65B). Next, speed conversion of this difference value is effected (step 65C). The difference (step 65D) between the target speed thus obtained and the speed (step 65G) obtained by converting the feedback position to the speed is applied to the driving system to drive the motor (step 65E). The position of the driving system is monitored by the position counter 65F, and the result of this monitoring is utilized as a feedback position. In this way, convergence to the target position can be accomplished.

Next, still another embodiment of the invention, wherein treatment is carried out while detecting a position error in the irradiating direction of the radiation and correcting the position of the collimator, will be explained.

Figures 9, 11:
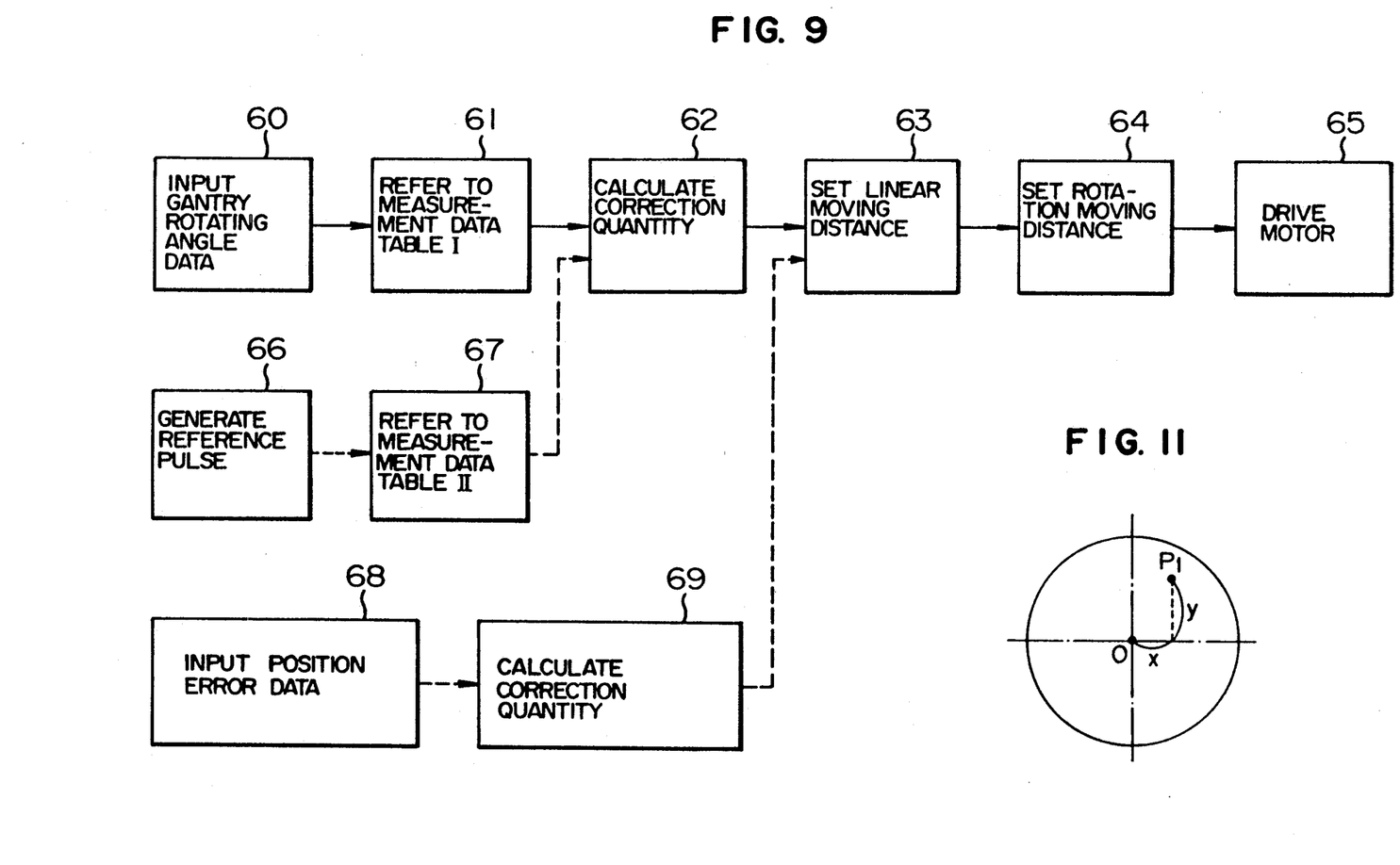
FIG. 9 is an explanatory view showing an operation of a collimator position controller.
FIG. 11 is a view showing a beam reception plane of a beam reception device.
Figure 10:
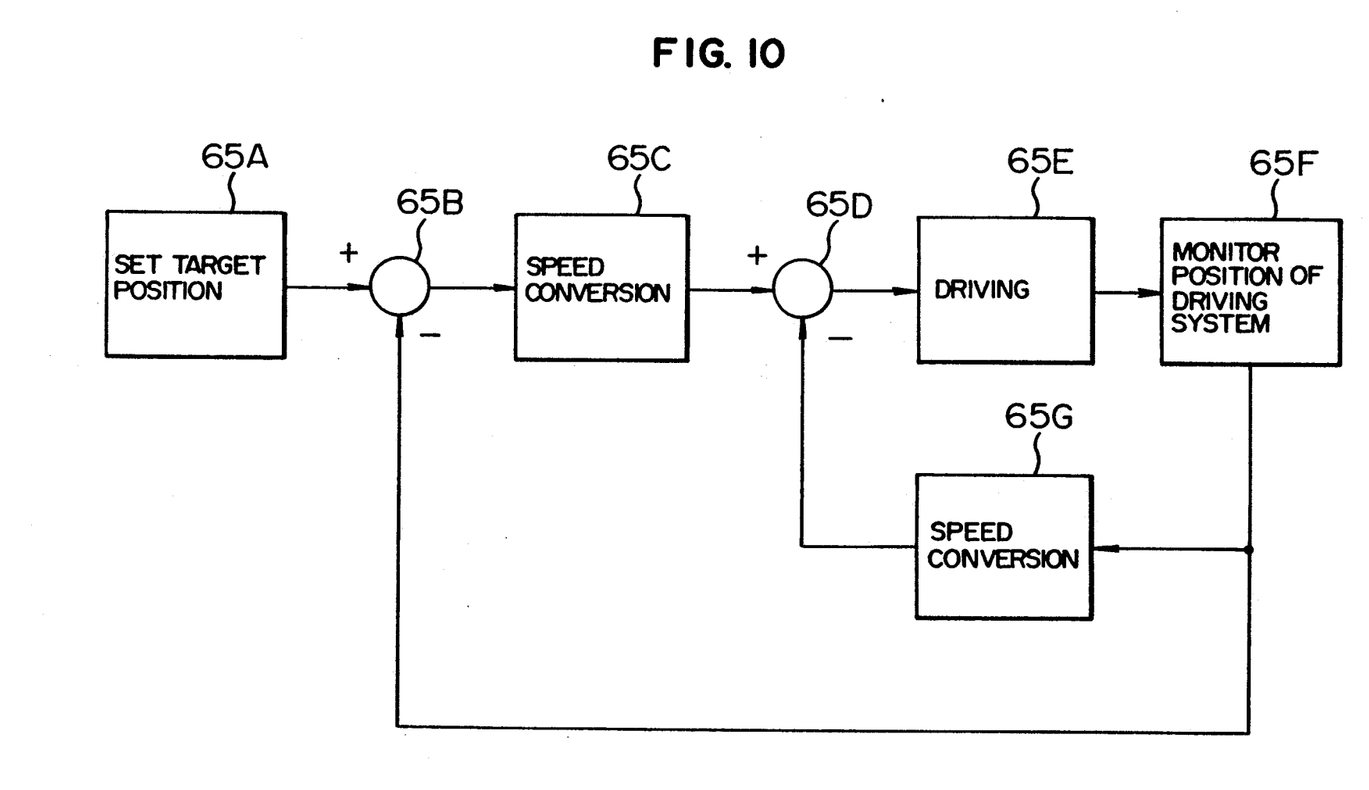
FIG. 10 is an explanatory view useful for explaining a control sequence of collimator driving motor.

FIG. 11 shows an example of the beam reception plane of the beam reception device 102 shown in FIG. 3. Assuming that the irradiation head 10 undergoes deflection and the laser beam from the laser generator 101 deviates from the reference point "O" to a point "$P_1$", then, the data relating to this deviation quantity such as x and y values of two-dimensional data shown in FIG. 11, for example, is inputted to the collimator position controller 104 from an optical spot position sensor 103 (step 68).

The collimator position controller 104 determines a correction value for offsetting this position error from the two-dimensional data (step 69). The subsequent operations are carried out on the basis of the steps 63 to 65 described above.

Next, the operation of the collimator position controller 104 when the position of the collimator is controlled in match with the motion of the focus that moves with the respiration, will be explained with reference to FIG. 9.

In this embodiment, dynamic data of the focus during a stable respiration of the patient is measured beforehand with respect to certain reference points (e.g. maximum exhalation point and maximum inspiration point) for the focus that moves with the respiration, too, and is stored as a data table II in the memory. Furthermore, a respiration sensor which detects at least one point in each cycle of the respiration cycles is situated. When the radiation is irradiated, the patient is placed on the treatment couch under the stable respiration state, and while certain reference pulses are being generated (step 66) in alignment with the reference points at the time of measurement described above during the detection of the respiration of the respiration by the respiration sensor, the measurement data is read out from the data table II in synchronism with the reference pulses (step 67). While the motor is controlled in the same way as described above (steps 62 to 65), the collimator is operated in synchronism with the respiration by the use of the driving apparatus 18 described already.

When the respiration synchronization irradiation is effected while the gantry is being rotated, the data are read out from both measurement tables I and II and after the correction is made, the motor is driven.

When the position error is detected in the irradiating direction of the radiation while treatment is being carried out, accurate correction can be made by moving the reference point "O" on the light reception device 102 in synchronism with the respiration of the patient during the calculation at the step 62.

When a radiation detector 135 such as a portal image system capable of inspecting the focus in such a manner as to oppose the irradiating direction of the radiation is situated, the motion of the focus moving with the respiration can be inspected, and the position of the collimator can be so controlled as to follow up the motion of the focus by the use of the driving apparatus 18.

There is another embodiment in the case in which the focus moves. In this embodiment, the movement of the focus is cancelled by moving the table 9.

The operations of this embodiment will be explained with reference to FIG. 8. The amount of the movement of the focus which is read out from the data table II or a position of the focus which is detected in a real time by a radiation detector 136 is inputted into a table controller 136. The table controller 136 is provided with a CPU and memories such as RAM and ROM, and has a function of operation. In the table controller 136, an amount of movement of the table 9 which is necessary to cancel the movement of the focus is calculated. The table 9 is moved by the table drive apparatus 137 according to the result of the calculation such that the line connecting a center portion of the focus and the apex of the radiation cone coincides with the center line of a hole of the collimator.

Next, still another embodiment of the present invention will be explained.

Figure 12:
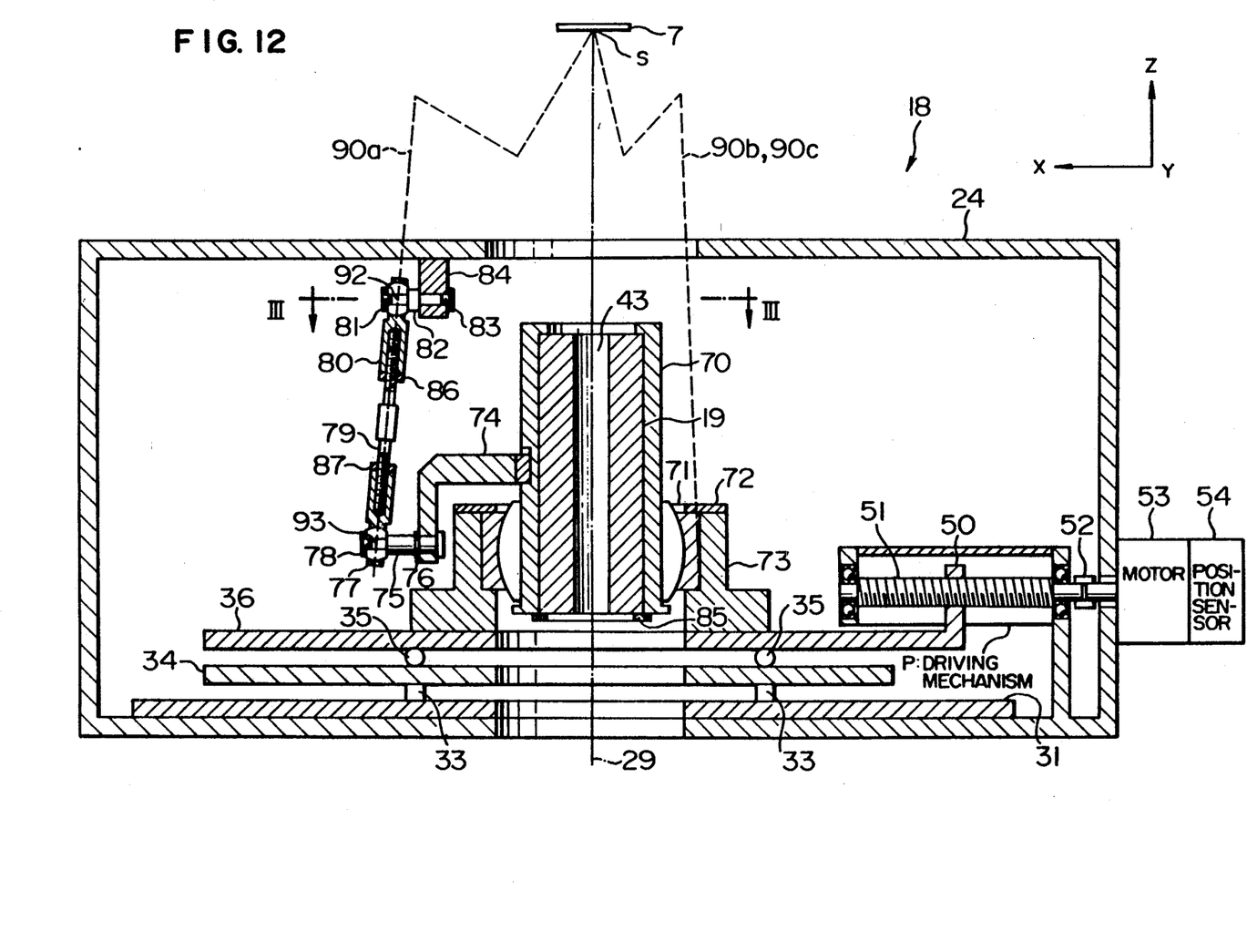
FIG. 12 is a sectional view showing another embodiment of the collimator and the driving apparatus.
Figure 13:
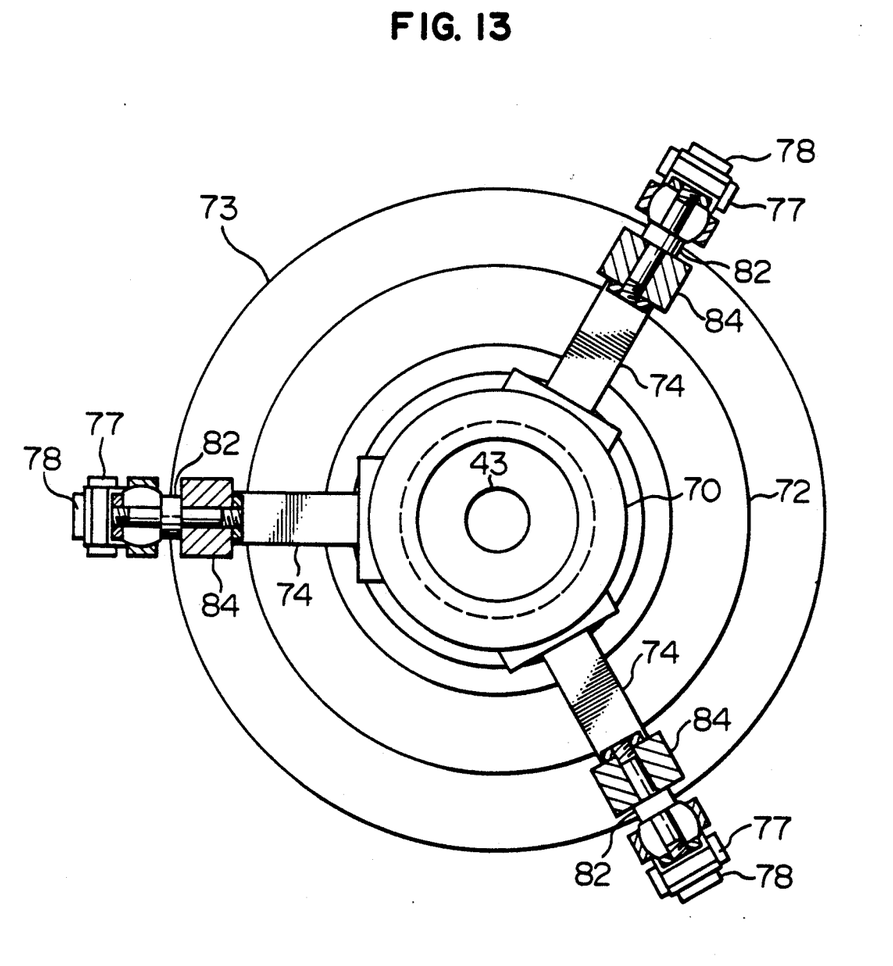
FIG. 13 is a sectional view taken along a line XIII—XIII of FIG. 12.

FIG. 12 is a sectional view showing another embodiment of the collimator and that of the driving apparatus 18, and FIG. 13 is a sectional view taken along a line XIII—XIII of FIG. 12.

A driving mechanism P in this embodiment is analogous to that of the embodiment shown in FIG. 4, but a swing mechanism and a link mechanism for moving the collimator in such a manner as to be capable of swinging two-dimensionally are different.

The swing mechanism comprises a bearing member 73 fixed onto the member 36 and supporting the spherical bearing 71, and a cylindrical member 70 having an outer diameter substantially equal to the inner diameter of the spherical bearing 71 and supporting the collimator 19.

The link mechanism comprises a bearing member 84 fixed to the casing 24 and supporting a shaft 82, a first rod end 80 having a spherical bearing fitting to the shaft 82, an arm 74 fixed to the cylindrical member 70, a shaft 75 having an outer diameter substantially equal to a hole bored in the arm 74, a second rod end 77 hiving a spherical bearing fitting to the shaft 75, and a shaft 79 connecting the first rod end 80 to the second rod end 77. Nuts 81 and 83 are fitted to fasten the first rod end 80, nuts 86 and 87 are fitted to fasten the shaft 79, and a nut 78 and a snap ring 76 are fitted to fasten the second rod end 77.

Three link mechanisms are equidistantly situated on the collimator 19 as shown in FIG. 13 (only one being shown in the drawing with the other two omitted in the drawing) and support the collimator 19. The center shafts 90a, 90b and 90c of these three link mechanisms are situated in such a fashion that when the central axis of the hole 43 of the collimator 19 coincides with the perpendicular axis 16 (FIG. 3) passing through the isocenter 15, they pass through the apex S of the cone of the radiation.

Next, the operation will be explained.

When, for example, the member moves in the x direction by the linear guide roller 35, the collimator 19, too, moves in the x direction. In this case, the link mechanism interconnected and fixed to the cylindrical member 70 can swing in the form of an arc having its radius on a straight line connecting a support point 92 to a support point 93 and using the support point 92 as its center. Due to this motion, the collimator 19 inclines, and the swing mechanism having the spherical bearing 71 insures smooth inclination, These mechanisms allow the center line 29 of the collimator hole to always pass through the apex S of the cone of the radiation when the collimator 19 inclines.

Though the two members 34 and 36 constitute the X—Y table in this embodiment, a similar effect can be obtained by the use of one member so long as it permits two-dimensional sliding motion.

The collimator is controlled by the driving means comprising the link mechanism and the positioning mechanism, but these link mechanism and positioning mechanism are not particularly limited. Though the X-ray is a typical example of the radiation, an electron beam and other radiations can also be used besides the X-ray. Furthermore, the axis of rotation of the gantry and that of the treatment couch exist round the horizontal axis and the perpendicular axis, but it may exist on an arbitrary plane.

We claim:

1. A stereotactic radiosurgery comprising:
   (a) a gantry rotating on a predetermined plane with an isocenter being a center thereof;
   (b) an irradiation head for irradiating a radiation in a direction of a center portion of a focus, supported by said gantry;
   (c) a collimator movably situated to said irradiation head, and having a hole for guiding said radiation to said center portion of said focus;
   (d) driving means for changing a position of said collimator while keeping a position relation in which a line connecting an apex of a radiation cone and said center portion of said focus coincides with a center line of said hole of said collimator;
   (e) means for detecting a position error between an irradiating direction of said radiation and said center portion of said focus; and
   (f) control means for moving said collimator to a position at which said detected position error is offset, by operating said driving means.

2. A stereotactic radiosurgery according to claim 1, wherein said driving means includes:
   a base situated in parallel with a horizontal plane and slidable two-dimensionally;
   means for sliding said base;
   swing means supported by said base, for allowing said collimator to swing two-dimensionally; and
   at least three link means for supporting said collimator, each of said link means situated in such a fashion that a central axis thereof passes through said apex of said radiation cone.

3. A stereotactic radiosurgery according to claim 2, wherein said swing means includes a spherical bearing.

4. A stereotactic radiosurgery according to claim 1, wherein said means for detecting said position error includes:
   a memory for storing a relation between a rotating angle of said gantry measured in advance and a position error in the radiation irradiating direction at said rotating angle as a table; and
   means for reading out a position error corresponding to data of said rotating angle inputted from said memory by receiving the data of said rotating angle of said gantry.

5. A stereotactic radiosurgery according to claim 1, wherein said means for detecting said position error includes:

optical beam generation means fitted to said irradiation head or a portion in the proximity of said irradiation head; and beam reception means for receiving said optical beam, so situated as to oppose said optical beam generation means with a predetermined gap between them.

6. A stereotactic radiosurgery according to claim 1, wherein said means for detecting said position error includes means for detecting a position error between said center portion of said focus and a center line of said hole of said collimator due to movement of said focus.

7. A stereotactic radiosurgery according to claim 6, wherein said position error detection means includes:

a memory storing a relation between movement of said focus measured in advance and the center line of said hole of said collimator as a table;

means for monitoring movement of said focus; and means for reading out a position error corresponding to a monitored position of said focus from said memory in response to an output of said monitor means.

8. A stereotactic radiosurgery according to claim 7, wherein said monitor means includes a respiration sensor for detecting a respiration state.

9. A sterotactic radiosurgery according to claim 6, further comprising means for moving a table on which a patient lies according to an output of said means for detecting position error due to said movement of said focus.

10. A stereotactic radiosurgery according to claim 1, wherein said means for detecting position error comprises means for detecting radiation, situated under the patient.

* * * * *